(12) United States Patent
Holzner et al.

(10) Patent No.: US 7,623,693 B2
(45) Date of Patent: Nov. 24, 2009

(54) METHOD AND APPARATUS FOR PRODUCING DATASETS FOR MAKING DENTAL PROSTHESES

(75) Inventors: Stephan Holzner, Hohenschaftlam (DE); Gerhard Weber, Inning Am Ammersee (DE)

(73) Assignee: Institut Straumann AG, Basel (CH)

( * ) Notice: Subject to any disclaimer, the term of this patent is extended or adjusted under 35 U.S.C. 154(b) by 736 days.

(21) Appl. No.: 11/254,033

(22) Filed: Oct. 19, 2005

(65) Prior Publication Data

US 2006/0093204 A1 May 4, 2006

(30) Foreign Application Priority Data

Oct. 20, 2004 (DE) .................. 10 2004 051 165

(51) Int. Cl.
*G06K 9/00* (2006.01)
*A61C 3/06* (2006.01)
*G06T 15/00* (2006.01)

(52) U.S. Cl. .................. 382/128; 382/154; 433/167; 345/419

(58) Field of Classification Search ......... 382/128–132, 382/145, 100, 154; 128/920–925; 250/455.11; 356/39, 12–19; 377/10–11; 600/300, 301; 345/419–428; 433/24, 213–219, 167
See application file for complete search history.

(56) References Cited

U.S. PATENT DOCUMENTS

| 5,027,281 | A  | * | 6/1991  | Rekow et al. ............... 700/182 |
| 5,224,049 | A  | * | 6/1993  | Mushabac ................... 700/163 |
| 7,058,213 | B2 | * | 6/2006  | Rubbert et al. .............. 382/128 |
| 7,110,594 | B2 | * | 9/2006  | Jones et al. ................. 382/154 |
| 2001/0038705 | A1 | * | 11/2001 | Rubbert et al. .............. 382/128 |

FOREIGN PATENT DOCUMENTS

EP  0 731 673 B1  9/1996
EP  0 913 140 A2  5/1999

* cited by examiner

*Primary Examiner*—Samir A. Ahmed
*Assistant Examiner*—Mehdi Rashidian
(74) *Attorney, Agent, or Firm*—Marshall, Gerstein & Borun LLP

(57) ABSTRACT

A method and apparatus for producing data for making dental prostheses, wherein the data can be produced on the basis of a model (2) which comprises individual segments (3*a*, 3*b*, 3*c*, ... ), such as representing a tooth, a preparation, a gingival area, a tooth gap or a small group of teeth, from different directions in space, and a storing device for storing the shape data obtained thereby, and—second shape data (12) of only the one segment (3*a*, 3*b*, 3*c*, ... ), only part of the segment (3*a*, 3*b*, 3*c*, ... ) being scanned, and the segment (3*a*, 3*b*, 3*c*, ... ) being arranged in a fixed orientation relative to a reference, and b) a comparing device for comparing the first and second shape data (1, 12) to determine the orientation of the first shape data (1) relative to the reference.

11 Claims, 6 Drawing Sheets

METHOD AND APPARATUS FOR PRODUCING DATASETS FOR MAKING DENTAL PROSTHESES

REFERENCE TO RELATED APPLICATION

This disclosure claims priority to German Application No. 102004051165.9, filed Oct. 20, 2004. The entire text of the priority application is incorporated herein by reference in its entirety.

FIELD OF DISCLOSURE

The present invention relates to a method and an apparatus for producing data for making dental prostheses and to a method for making dental prostheses.

It is known from EP 0 731 673 B1 that dental structures of a model are first leveled to determine the mutual positions of the structures in the model and to find an appropriate position for subsequent scanning, so that during scanning specific areas do not remain inaccessible for scanning due to undercuts.

A drawback is here that a leveling device is very expensive because both positions and inclinations of a platform must be sensed and the sensors needed therefor are quite expensive.

Furthermore, EP 0 913 140 discloses a method and an apparatus for making a dental prosthesis. A duplicate is here divided into duplicate sections and the shape of the individual duplicate sections is determined.

To determine the relative arrangement of the individual duplicate sections relative to one another, the overall shape of the duplicate itself must also be determined, but with less accuracy as a large area must be measured. The data of the duplicate sections are then fitted into the coarse data of the duplicate in a matching process.

It is here disadvantages that the resolution of the data of the duplicate, i.e. the data obtained by scanning a relatively large area, does not show the desired high precision, so that a certain inaccuracy may be observed with dental prostheses extending over a large area. This yields dental prostheses that do not always optimally match the model or a residual dental area.

SUMMARY OF THE DISCLOSURE

It is therefore an object of the present disclosure to provide a method and an apparatus in which data that are as accurate as possible can be obtained at costs that are as low as possible for making dental prostheses.

It is a further object to provide a method for making dental prostheses that provides dental prostheses that are as accurate as possible at costs that are as low as possible.

Instead of a scanning operation with reduced resolution in which the shape of a duplicate is sensed, only part of a segment is scanned in the method, but the orientation of the segment relative to a reference, for example a special coordinate system, is fixed.

A segment may represent an individual dental location or also a small group of dental locations. Each dental location may represent an individual tooth, a preparation, an implant, a gingival area, a tooth gap, or the like.

The orientation of the segment may e.g. be known in that the segment is moved with a controlled positioning to a specific location of the scanning area.

In another step, a set of shape data of the segment that is as comprehensive as possible is obtained from each segment individually by scanning the segment from different directions in space. The first shape data that describe a segment as comprehensively as possible in its shape can now be compared with the second shape data in the case of which only part of a segment has been scanned so as to determine an orientation of the first shape data relative to the reference.

The first shape data can first be obtained and then the second shape data, or the second shape data are first obtained and then the first shape data. It is also possible to carry out the two operations at the same time on the basis of two identical models.

In an advantageous embodiment, a two-dimensional view of a model is taken, on the basis of which the position of the various segments is determined. Only data that show the position of the segments are stored. These may e.g. be data identifying an area in a two-dimensional top view. This may e.g. be an angular area, a rectangle, a trapezoidal area, or the like.

With this information indicating the area in which a segment is positioned, the corresponding segment can be moved as perfectly as possible into the scanning area of a scanning device. That scanning device will then determine the second shape data with a resolution that is as high as possible. After the first and second shape data of a segment have been compared, the second shape data need not be stored.

If the second shape data are determined in a position different from the top view, it is advantageous when a controllable holder is used for moving from the model from the one position in the other position because an exact positioning of the model in the scanning region will then be possible. Scanning can be performed optically or mechanically.

In the method for making dental prostheses, a dental prosthesis is produced with the data obtained. This can be done by corresponding milling or the like, in which the dental prosthesis is milled out of the material.

The apparatus comprises a scanning device with which first shape data of an individual segment can be determined. The first shape data determined in this process can be stored and second shape data of only that segment can be determined with the scanning device, the orientation of the segment being however fixed relative to a reference.

Different scanning devices or the same scanning device may be provided for determining the first and second shape data.

Furthermore, the apparatus comprises a comparing device for comparing the first and second shape data to determine the orientation of the first shape data relative to the reference.

BRIEF DESCRIPTION OF THE DRAWINGS

An embodiment of the method of the disclosure and the apparatus of the invention disclosure shall now be explained with reference to the attached figures, of which.

DETAILED DESCRIPTION OF THE DISCLOSURE

Figure 1A:
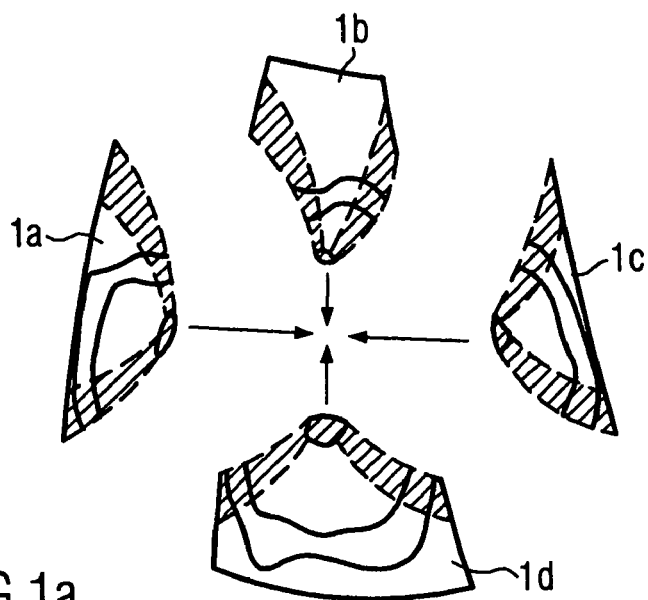
FIG. 1a shows four individual data sets obtained by linearly scanning a segment.

FIG. 1a shows four individual data sets 1a to 1d which were obtained by linearly scanning a segment representative of a tooth. The four datasets 1a to 1d were obtained by scanning the segment from different directions in space. For scanning the segment from different directions in space the segment was each time rotated relative to a scanning device.

The hatched areas are overlap areas used to interconnect the four individual datasets 1a to 1d in order to obtain an individual dataset in this way.

Figure 1B:
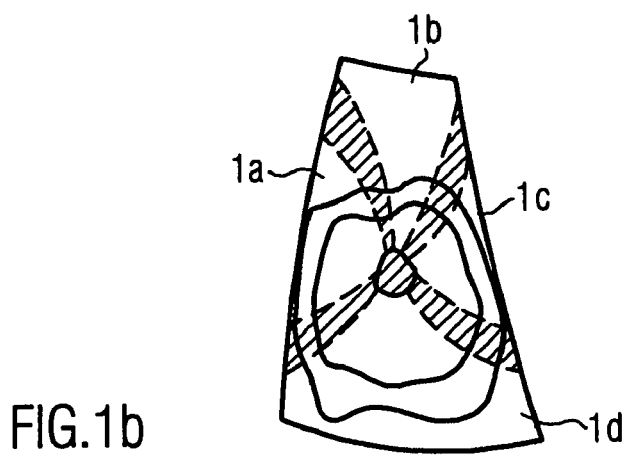
FIG. 1b illustrates how the four individual datasets are overlapped on the overlap regions.

FIG. 1b) shows how the four individual datasets are overlapped on the overlap regions.

Figure 1C:
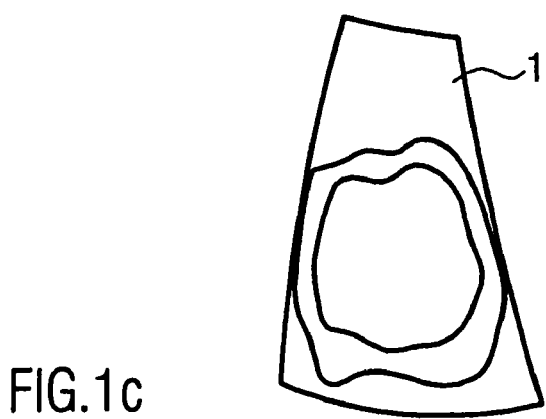
FIG. 1c shows the resulting overall view, which corresponds to the first shape data.

FIG. 1c) shows the resulting overall view, which corresponds to the first shape data.

Since the segment was scanned from different directions in space, its shape is known as comprehensively as possible, and there are no unscanned undercuts or similar unscanned regions.

The first shape data 1a to 1d can e.g. be determined by optical scanning. The segment is here shifted relative to the scanning device and a profile is each time recorded along a line and stored. When put together the different yields the two-dimensional datasets shown in FIG. 1a).

In FIG. 1, the datasets can just be shown in a two-dimensional view, but in the method the surface is recorded in three dimensions and stored.

Figure 2A:
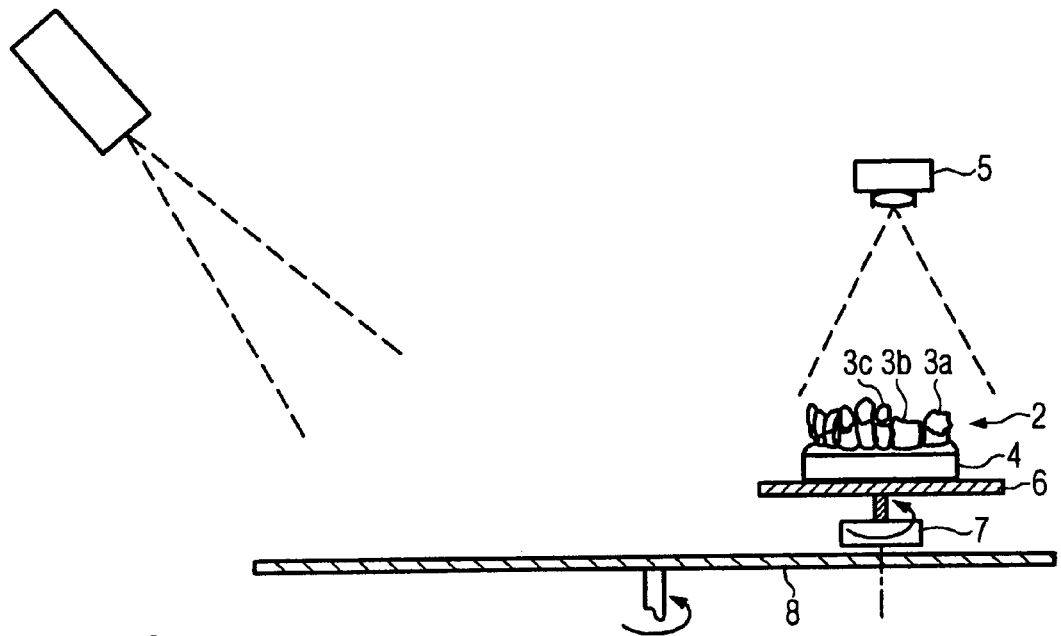
FIG. 2a is a schematic illustration of an apparatus for producing data for making dental prostheses, wherein a model is positioned under a camera.

FIG. 2a) shows an apparatus in which a model 2 with segments 3a, 3b, 3c, ... is illustrated. The individual segments 3a, 3b, 3c, ... can be removed from a base 4 individually.

The model 2 is positioned underneath a camera 5 with which a two-dimensional top view on the model can be taken. The model 2 is positioned on a rotary table 6 which while being e.g. controlled by a servomotor 7 can be rotated. For fixing a zero position a magnet, for example, may be provided on the rotary table, or also a pair of magnets with which the rotary table 6 can be pulled by magnetic force into a definite position if the rotary table is freely movable.

The table 6, in turn, is arranged on a rotary table 8 which while being also controlled, for example by a stepped motor, can be rotated, and the zero position of which can be fixed (e.g. with a magnet).

Figure 2B:
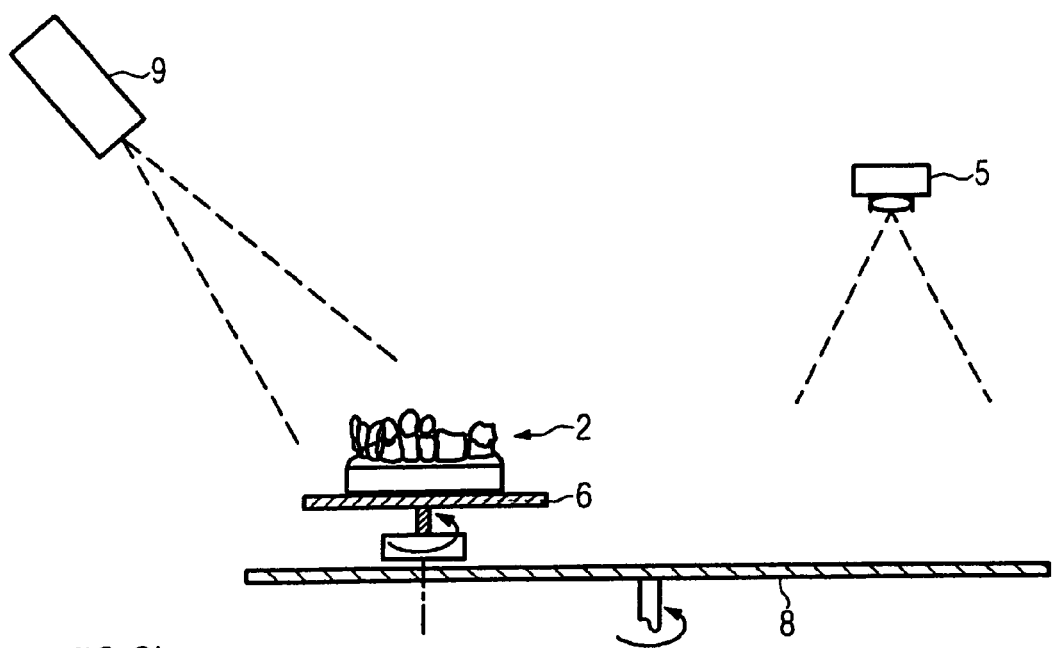
FIG. 2b is a schematic illustration of an apparatus FIG. 2a wherein the model is positioned under a scanning device.

As shown in FIG. 2b), the table 8 was rotated such that the model is positioned in a scanning area of a scanning device 9.

Figure 2C:
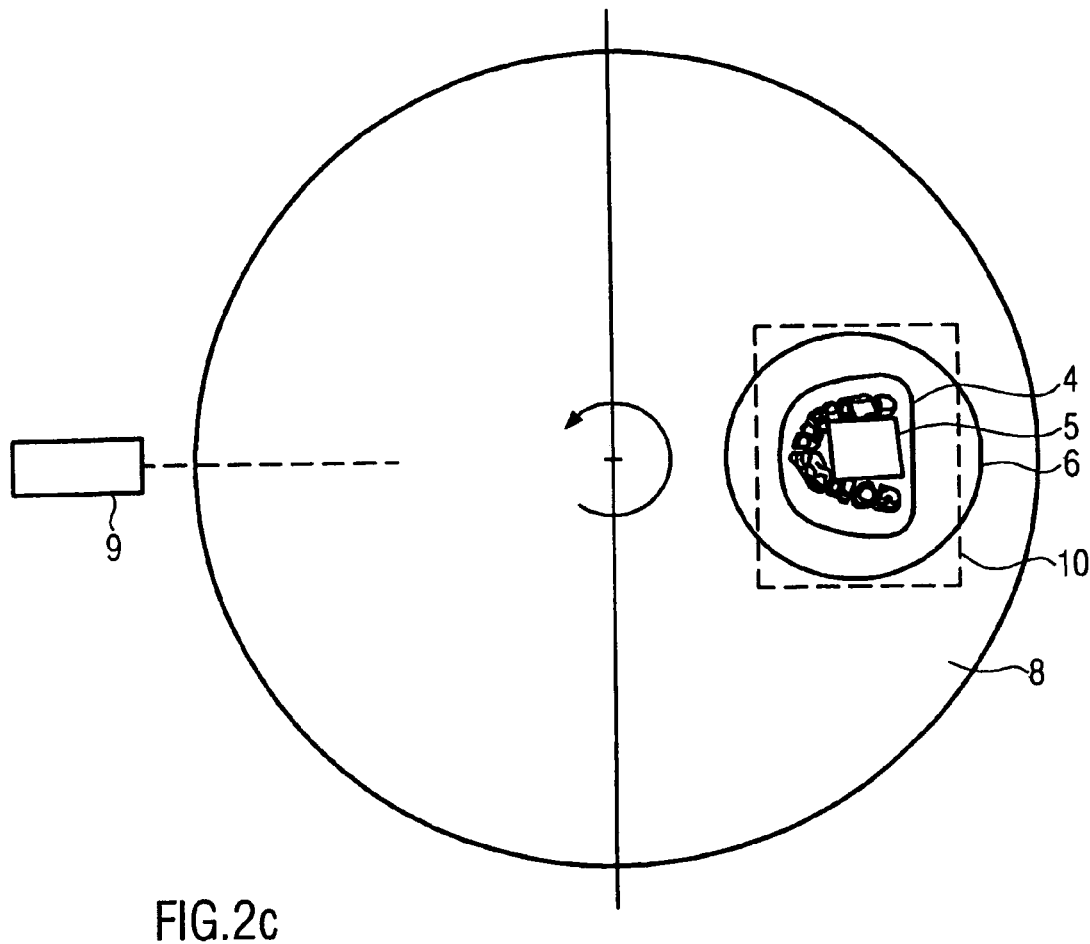
FIG. 2c is a top view of the apparatus of FIG. 2a wherein the model is positioned under the camera.

FIG. 2c) is a top view on which the model 4 is located in the recording area 10 of the camera 5.

Figure 3:
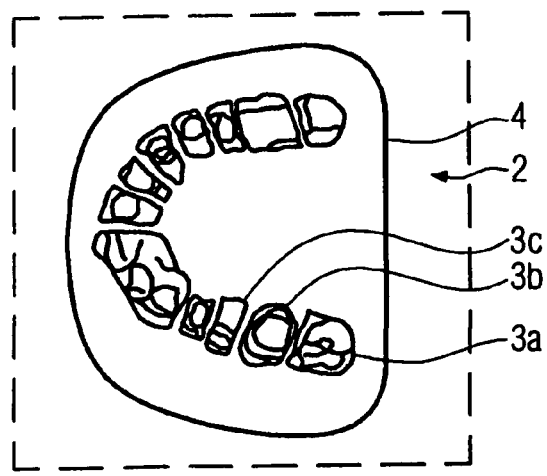
FIG. 3 is a two-dimensional top view of the model.

FIG. 3 is an enlarged view of a picture as can be taken of the model 2 with the camera 5.

Figure 4A:
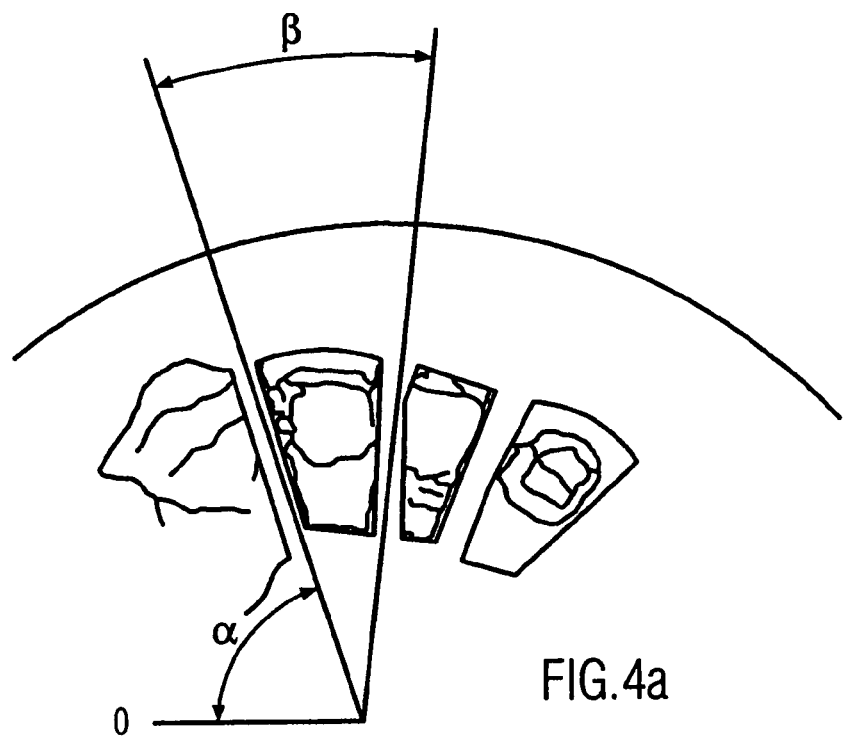
FIG. 4a is a top view of the model and the angles indicating a position of a segment of the model.
Figure 4B:
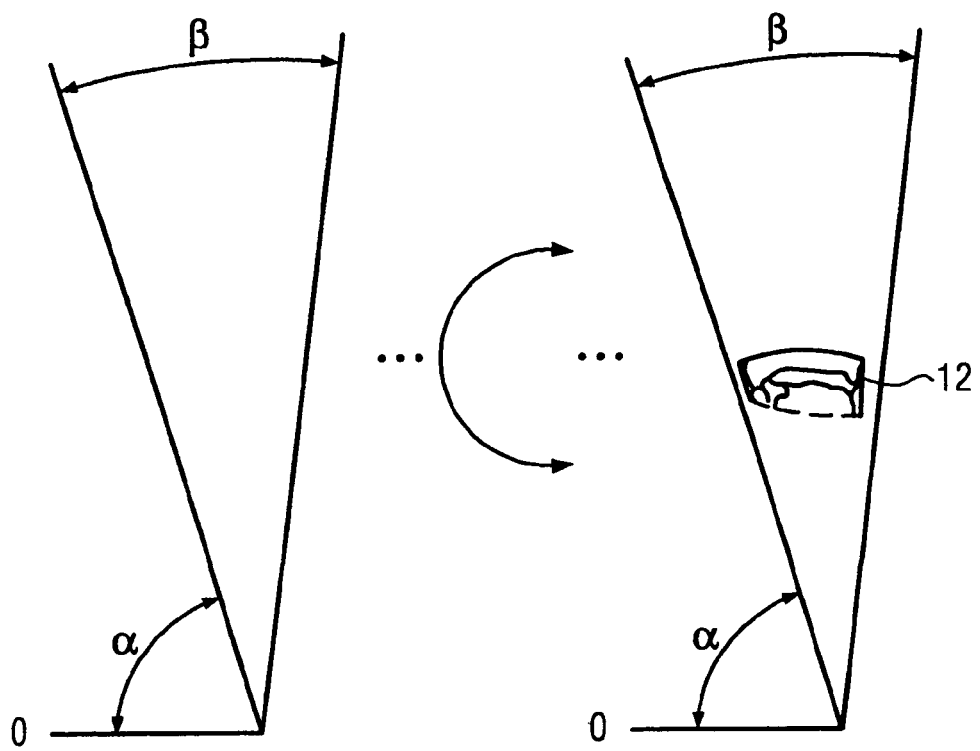
FIG. 4b illustrates the angles used to describe the position of an area (left), and the angles indicating the position of the second shape data (right)

The determination of the second shape data shall be explained with reference to FIGS. 4 and 5. The image shown in FIG. 3 is processed by way of image recognition such that the position of the individual segments is recognized.

The data which indicate the position of the area in which the segment is located are stored for each segment. FIG. 4a) shows, for example, an angle α and an angle β. Angle α indicates the position of a straight line relative to a reference line designated by 0. Angle β indicates the width of the area in angle coordinates. The position of the area can be described by angles α and β. Consequently, only angles α and β are stored for the associated area of a segment.

It is also possible to indicate translational coordinates instead of angle coordinates, or a mixture of both. The model is thus schematically divided into two individual areas without the need for storing the top view itself of large amounts of data. Only the coordinate data of the individual areas are stored.

Figure 5A:
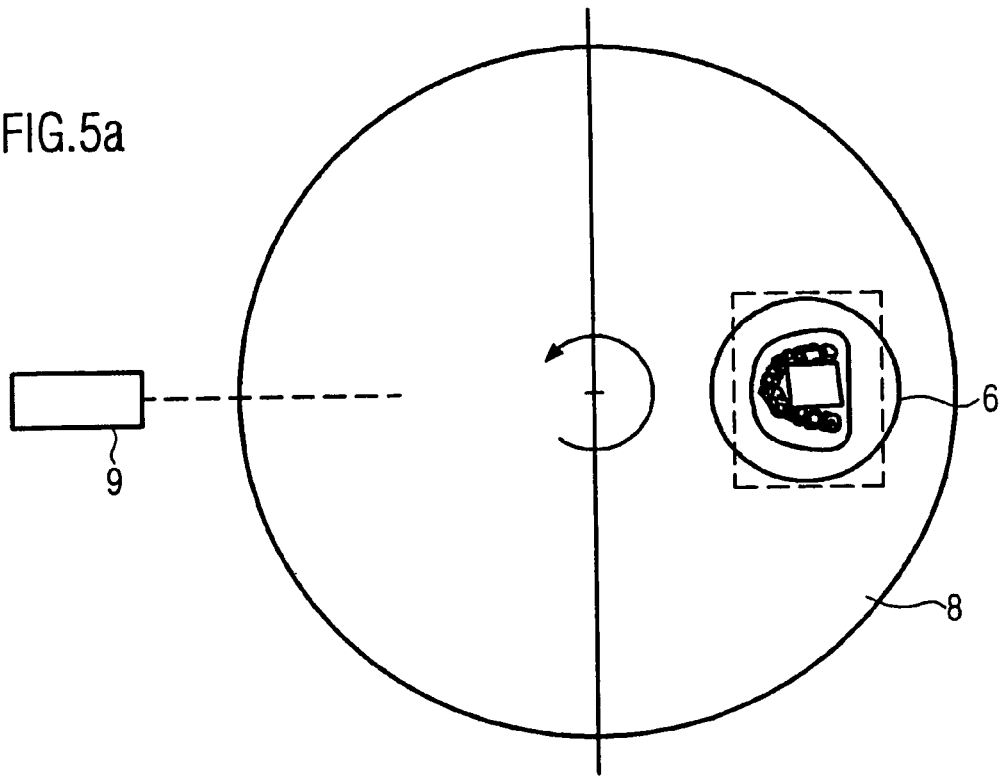
FIG. 5a is a top view of the apparatus of FIG. 2a wherein the model is positioned under the camera.

As is once again shown in FIG. 5a (identical with FIG. 2c), the position of the individual areas relative to the rotary table 6 is thus known.

Instead of a division into individual areas on the basis of the recording made with a camera, a division without a camera is also possible. For instance an index line may be provided on the table 6 or in a glass pane above the table and the model should then be arranged in a predetermined position relative to said index line. A stop or any other adjusting aid may here be used as well. It is also possible to arrange the model with a corresponding adjusting aid on the table 6 in such a manner that the center of a circular arc on which the positions of the incisors are located is fixed at a specific location of the table 6. The orientation may then be chosen in a specific predefined way, for example in such a manner that the positions of the incisors are oriented towards the rotational axis of the table 8.

The division into areas is then carried out automatically on the basis of a predetermined pattern. It is here still possible to have a corresponding division checked by an operator. To this end the areas may e.g. be moved in successive order into corresponding predetermined positions to see whether appropriate segments or parts of segments are positioned in the corresponding areas.

Figure 5B:
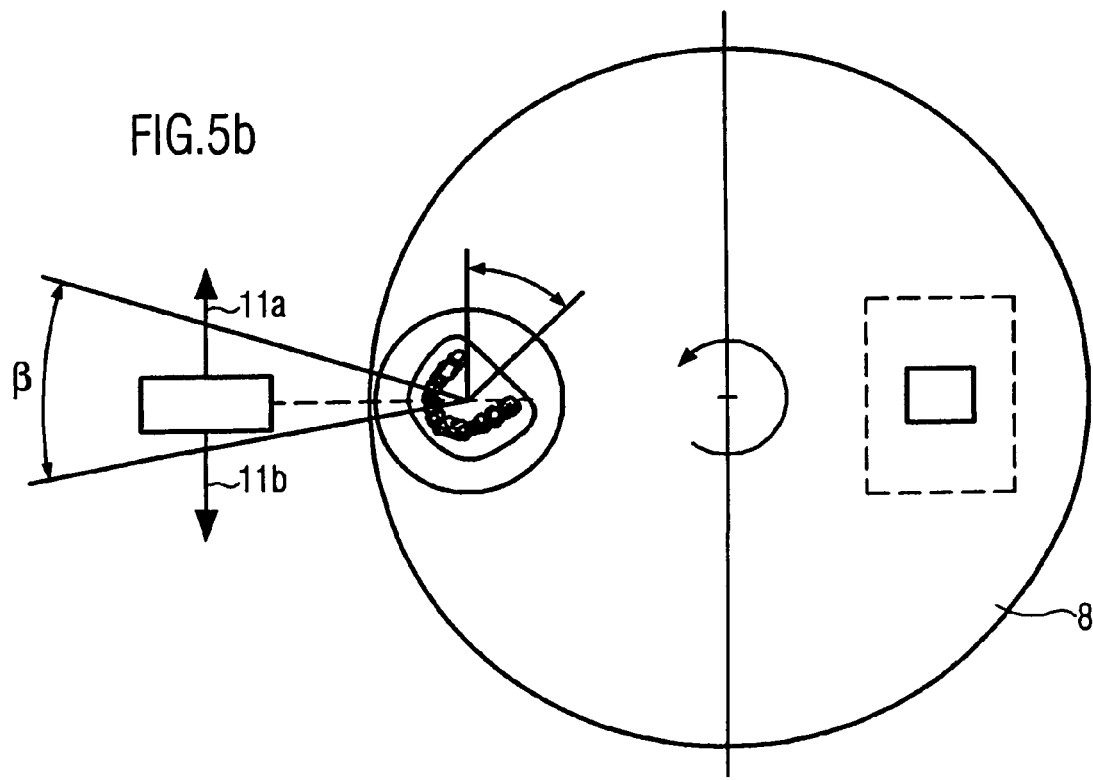
FIG. 5b is a schematic illustration of the apparatus of FIG. 2a wherein a scanning area of the scanning device is shown.

After division of the top view into the individual areas, the rotary table 8 is rotated out of the position shown in FIG. 5a) into the position shown in FIG. 5b). For instance if the center of the camera 5 is opposite the center of the scanning area of the scanning device 0 at 180° if possible. The rotary table 6 is then rotated such that a previously determined area is positioned as completely as possible in the scanning area of the scanning device 9. The scanning area is schematically shown in FIG. 5b) by way of two arrows 11a and 11b. The size of the arrows is here however considerably exaggerated. It is thus possible by displacing the table 8 or the scanning device 9 relative to each other to scan part of the surface of the corresponding segment. However, a minor part of the segment is here accessible. To achieve a high resolution, only an individual segment or even only part thereof is here scanned. With a fixed geometrical arrangement between scanning head 9 and the rotary tables 6 and 8 and with the known position of the tables 6 and 8 it can be determined which shape is given in an area by a segment. Thanks to the exact positioning of the rotary table 6 and the rotary table 8 the position of an area relative to the scanning device is known and thus also relative to the other areas and to the base, respectively. It is thus exactly known at which place (with reference to a coordinate system), the surfaces are located that are scanned with the scanning device 9. The surface data obtained from an individual segment, in the case of which the position of the area is known, are the second shape data.

The comparison between the first and second shape data shall now be explained with reference to FIG. 6.

Figure 6A:
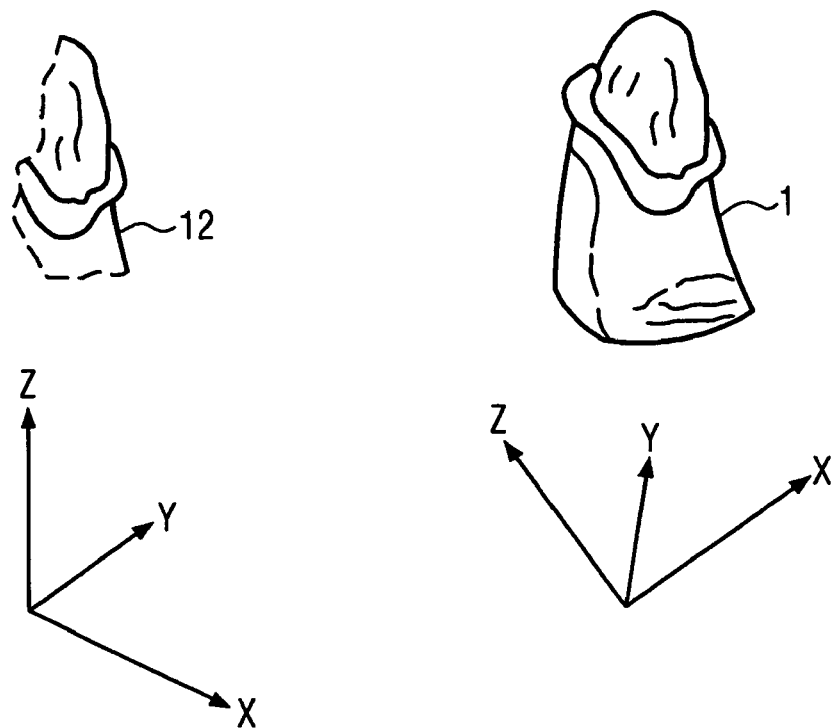
FIG. 6a is a schematic illustration of the comparison between the first and second shape data, wherein the orientation of the second shape data (left) is known relative to a coordinate system, and wherein the orientation of the first shape data (right) is not known relative to the coordinate system of the second shape data.

FIG. 6a) shows an image of the second shape data at the left side. These second shape data only show part of the shape of the segment, but with a high resolution in said area. Furthermore, the exact orientation of said surface relative to a coordinate system (a reference) is known.

Figure 6B:
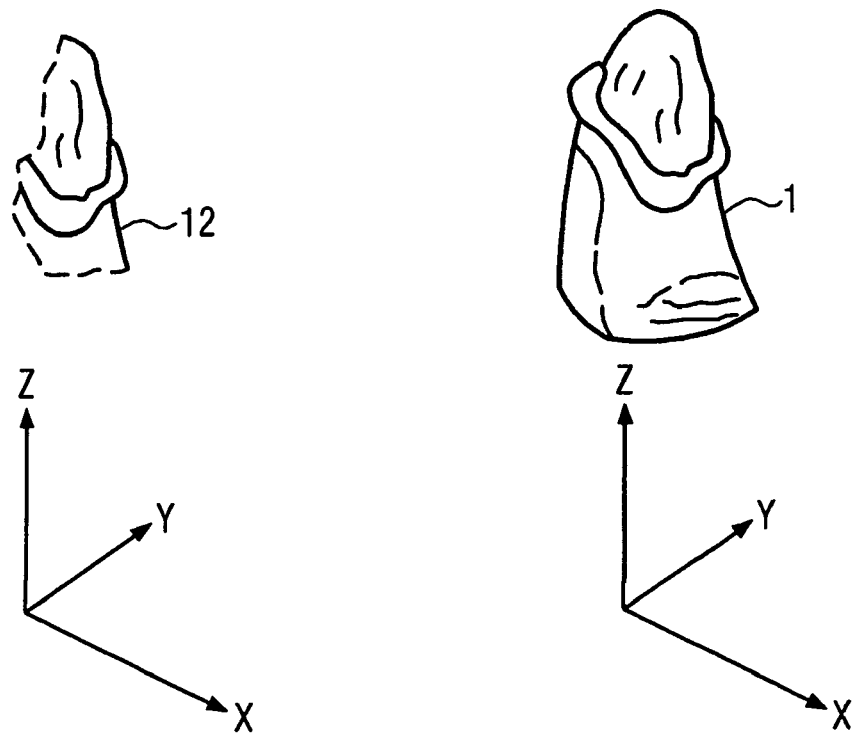
FIG. 6b is a schematic illustration of the comparison between the first and second shape data, wherein the first and second shape data of FIG. 6a are present in the same coordinate system.

The first shape data as shown in FIG. 6a) at the right side represent the complete shape of said segment. However, the coordinate system is unknown in comparison with the coordinate system of the second shape data. The set of first shape data can however be compared in a corresponding matching process with the second shape data such that both shape data are present in the same coordinate system, as shown in FIG. 6b). It is thus possible to give the high resolution first set of shape data its exact position relative to the coordinate system of the overall model.

When the previously described steps for the individual segments or areas are repeated, the data for making dental prostheses can thereby be obtained step by step.

Since the comparison of the first and second shape data said shape data normally derive from the same segment, a data comparison can be carried out relatively easily without any errors. By contrast, in the prior art in which the data of a duplicate section are combined with the data of a duplicate, it may easily happen that a data set of a duplicate section is not combined at the correct place with the data of the duplicate because implant posts, for instance, are in rotational symmetry and two or more implant posts can thus be confused easily when combined.

With the data obtained in this way the dental prostheses can then be made. This is possible with different materials, such as zirconium oxide, aluminum oxide ceramics, titanium, or a chromium cobalt alloy.

The bottom sides facing the residual dental areas can be shaped from respective blanks.

Hence, the apparatus of the disclosure comprises a scanning device with which the first shape data and second shape data can be determined.

A comparing device for comparing the first and second shape data is not illustrated in the figures, but is usually implemented by a corresponding computer.

The invention claimed is:

1. A method for producing data for making dental prostheses, wherein the data are produced on the basis of a model (2) which comprises individual segments located in different areas, each area comprising an individual segment, comprising the steps of:
   a) determining with a scanning device first shape data (1) of an individual segment (3a, 3b, 3c, . . . ), by scanning this individual segment (3a, 3b, 3c) from different directions in space, the resulting shape data being stored;
   b) determining with the scanning device second shape data (12) of this individual segment (3a, 3b, 3c, . . . ), wherein only part of this individual segment (3a, 3b, 3c, . . . ) is scanned, and wherein this individual segment (3a, 3b, 3c, . . . ) is arranged in a fixed orientation relative to a reference; and
   c) comparing by a comparing device the first and second shape data (12) to determine the orientation of the first shape data (1) relative to the reference,
   wherein a two-dimensional top view on the model (2) is recorded with a camera (5) and the position of the different areas is determined on the basis thereof, each of the areas comprising a segment, and angles α, β indicative of the position of each area being stored.

2. The method according to claim 1, wherein step a) is carried out before step b).

3. The method according to claim 1, wherein step b) is carried out before step a).

4. The method according to claim 1, wherein the determined position of the area is used for orienting the area when the second shape data (12) are determined.

5. The method according to claim 1, wherein the model (2) is moved with a controllable holder (8) between the position for recording the top view and the position for determining second shape data (12).

6. The method according to claim 1, wherein the model (2) is fixed in a predefined orientation relative to one of an index line, an index point and an adjusting aid on a holder (6).

7. The method according to claim 1, wherein the second shape data are not stored after step c).

8. The method according to claim 1, wherein the scanning operation for determining one of the first, second, and first and second shape data (1, 12) is carried out one of optically, mechanically, and a combination thereof.

9. A method for making a dental prostheses, wherein the data required therefore are produced with a method according to claim 1.

10. The method according to claim 1, wherein the individual segments represent a tooth, a preparation, a gingival area, a tooth gap, or a small group of teeth, preparations, or gingival areas.

11. An apparatus for producing data for making dental prostheses, wherein the data can be produced on the basis of a model (2) which comprises individual segments located in different areas, each area comprising an individual segment, and wherein the individual segments are representative of a tooth, a preparation, a gingival area, a tooth gap, or a small group of teeth, preparations, or gingival areas, the apparatus comprising:
   a) a scanning device (9) for determining:
      first shape data (1) of an individual segment (3a, 3b, 3c, . . . ) by scanning this individual segment (3a, 3b, 3c, . . . ) from different directions in space, and a storing device for storing the shape data obtained thereby, and
      second shape data (12) of this individual segment (3a, 3b, 3c, . . . ), wherein only part of this individual segment (3a, 3b, 3c, . . . ) is scanned, and wherein this individual segment (3a, 3b, 3c, . . . ) is arranged in a fixed orientation relative to a reference, and
   b) a comparing device for comparing the first and second shape data (1, 12) to determine the orientation of the first shape data (1) relative to the reference, and
   c) a camera for recording a two-dimensional top view on the model (2) and determining on the basis thereof the position of the different areas, each of the areas comprising a segment, and a storing device for storing angles α, β indicative of the position of each area.

* * * * *